United States Patent
Huizenga et al.

(10) Patent No.: US 10,035,744 B2
(45) Date of Patent: *Jul. 31, 2018

(54) PROCESS FOR THE SEPARATION OF GLYCOLS

(71) Applicant: SHELL OIL COMPANY, Houston, TX (US)

(72) Inventors: Pieter Huizenga, Amsterdam (NL); Kai Jürgen Fischer, Amsterdam (NL); Waldo Eugene De Villiers, Katy, TX (US); Karin Bus, Amsterdam (NL); Dorien Veldhuizen, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/524,276

(22) PCT Filed: Nov. 4, 2015

(86) PCT No.: PCT/EP2015/075678
§ 371 (c)(1),
(2) Date: May 4, 2017

(87) PCT Pub. No.: WO2016/071385
PCT Pub. Date: May 12, 2016

(65) Prior Publication Data
US 2017/0313640 A1    Nov. 2, 2017

(30) Foreign Application Priority Data

Nov. 6, 2014 (EP) .................... 14192153

(51) Int. Cl.
*C07C 29/86* (2006.01)
*B01D 11/00* (2006.01)
*B01D 11/04* (2006.01)

(52) U.S. Cl.
CPC .......... *C07C 29/86* (2013.01); *B01D 11/0426* (2013.01); *B01D 11/0492* (2013.01); *B01D 2011/002* (2013.01)

(58) Field of Classification Search
CPC ................................ C07C 29/86; B01D 11/00
USPC ....................................................... 568/868
See application file for complete search history.

(56) References Cited

U.S. PATENT DOCUMENTS

| 2011/0312050 A1 | 12/2011 | Zhang et al. |
| 2012/0184783 A1 | 7/2012 | Barnicki |
| 2013/0284584 A1 | 10/2013 | Xiao et al. |

FOREIGN PATENT DOCUMENTS

CN    102643165 B    7/2014

OTHER PUBLICATIONS

International Search Report and Written Opinion received for PCT Patent Application No. PCT/EP2015/075678, dated Dec. 10, 2015, 9 pages.

*Primary Examiner* — Sikarl A Witherspoon

(57) ABSTRACT

The invention provides a process for the separation of MEG and 1,2-BDO from a first mixture comprising MEG and 1,2-BDO in a first solvent by the steps of: (i) combining said first mixture with a second solvent stream comprising a second solvent in a first extraction column; (ii) recovering (a) a second mixture of MEG and 1,2-BDO in the second solvent, wherein the molar ratio of MEG:1,2-BDO is lower in the second mixture than in the first mixture; and (b) a solution comprising MEG in the first solvent; (iii) combining said second mixture with a first washing stream, said first washing stream also comprising the first solvent in a second extraction column; (iv) recovering (c) a first extract stream comprising the second solvent and 1,2-BDO and (d) a third mixture comprising MEG and, optionally, 1,2-BDO in the first solvent.

7 Claims, 2 Drawing Sheets

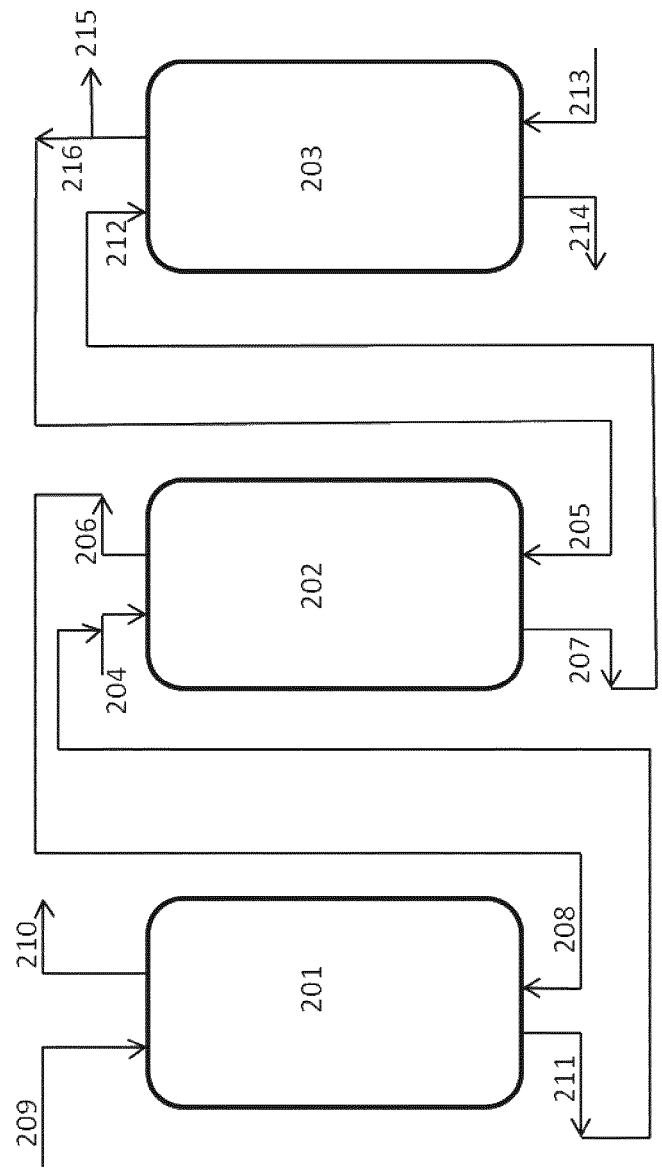

PROCESS FOR THE SEPARATION OF GLYCOLS

PRIORITY CLAIM

The present application is the National Stage (§ 371) of International Application No. PCT/EP2015/075678, filed Nov. 4, 2015, which claims priority from European Patent Application No. 14192153.6, filed Nov. 6, 2014 incorporated herein by reference.

FIELD OF THE INVENTION

The present invention relates to a process for the selective separation of glycols.

BACKGROUND OF THE INVENTION

Ethylene glycol and propylene glycol are valuable materials with a multitude of commercial applications, e.g. as heat transfer media, antifreeze, and precursors to polymers, such as PET. Ethylene and propylene glycols are typically made on an industrial scale by hydrolysis of the corresponding alkylene oxides, which are the oxidation products of ethylene and propylene, produced from fossil fuels.

In recent years, increased efforts have focused on producing chemicals, including glycols, from renewable feedstocks, such as sugar-based materials. For example, US 2011/312050 describes a continuous process for the catalytic generation of polyols from cellulose, in which the cellulose is contacted with hydrogen, water and a catalyst to generate an effluent stream comprising at least one polyol.

CN 102643165 is directed to a catalytic process for reacting sugar in an aqueous solution with hydrogen in the presence of a catalyst in order to generate polyols.

As with many chemical processes, the reaction product stream in these reactions comprises a number of desired materials, diluents, by-products and other undesirable materials. In order to provide a high value process, the desirable product or products must be obtainable from the reaction product stream in high purity with a high percentage recovery of each product and with as low as possible use of energy and complex equipment.

In known processes to make glycols, the glycols are usually present at high dilution in a solvent, typically water. The water is usually removed from the glycols by distillation. Subsequent purification of the glycols is then carried out by fractional distillation. This process can have high costs both in terms of capital and operational expenditure. Further, repeated heating or maintenance at raised temperatures in the distillation steps may also lead to decomposition of the desired glycol products.

When glycols are produced by hydrogenolysis of sugars, a mixture of glycols is produced. The main glycol constituents in the reaction product stream are monoethylene glycol (MEG), monopropylene glycol (MPG) and 1,2-butanediol (1,2-BDO). The separation of these glycols by fractional distillation is complicated due to the similarity in boiling points, particularly between MEG and 1,2-BDO (respectively 197 and 196° C.). Further, the isolation of a pure MEG overheads stream by fractional distillation from a mixture comprising MEG and 1,2-BDO is made impossible by the formation of an azeotrope between MEG and 1,2-BDO.

US 2012/0184783 discloses several methods for the extraction of glycols from aqueous streams. This document discloses methods for the selective extraction of individual glycols from concentrated mixtures thereof comprising less than 50 wt % water. Further embodiments are also disclosed in which all glycols are extracted together from a more dilute aqueous stream also containing glycerol or glucose.

It would, therefore, be advantageous to provide an improved method suitable for the recovery of individual glycols from mixtures of two or more glycols, particularly MEG and 1,2-BDO.

SUMMARY OF THE INVENTION

Accordingly, the present invention provides a process for the separation of MEG and 1,2-BDO from a first mixture comprising MEG and 1,2-BDO in a first solvent by the steps of:
(i) combining said first mixture with a second solvent stream comprising a second solvent in a first extraction column;
(ii) recovering (a) a second mixture of MEG and 1,2-BDO in the second solvent, wherein the molar ratio of MEG:1,2-BDO is lower in the second mixture than in the first mixture; and (b) a solution comprising MEG in the first solvent;
(iii) combining said second mixture with a first washing stream, said first stream also comprising the first solvent in a second extraction column;
(iv) recovering (c) an extract stream comprising the second solvent and 1,2-BDO and (d) a third mixture comprising MEG and, optionally, 1,2-BDO in the first solvent

BRIEF DESCRIPTION OF THE DRAWINGS

FIGS. 1 and 2 are schematic diagrams of exemplary, but non-limiting, embodiments of a process for the separation of glycols as described herein.

DETAILED DESCRIPTION OF THE INVENTION

Figure 1:
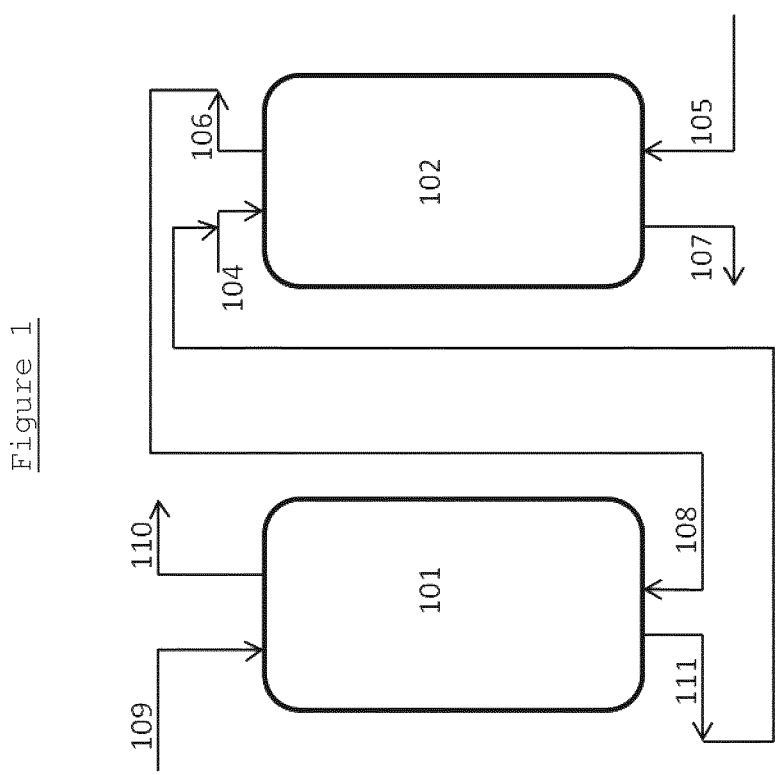

The present inventors have found that MEG and 1,2-BDO can be effectively separated from a mixture comprising these two materials in a first solvent by contacting the mixture with a second solvent in a first extraction column and producing a second mixture of a portion of the MEG and substantially all of 1,2-BDO in the second solvent. Washing the second mixture with a stream comprising the first solvent then allows the MEG (and, optionally, some of the 1,2-BDO) present in this second mixture to be washed out into the stream of the first solvent to provide a first extract stream comprising 1,2-BDO in the second solvent. Thus, MEG and 1,2-BDO can be separated from each other in a facile process.

Preferably, the first mixture comprising MEG and 1,2-BDO in a first solvent is derived from the reaction product stream from a process for the production of glycols. In a particularly preferred embodiment of the invention, the first mixture comprising MEG and 1,2-BDO in a first solvent is derived from the reaction product stream from a process for the hydrogenolysis of a saccharide-containing feedstock.

Typically, the reaction product stream from a process for the hydrogenolysis of a saccharide-containing feedstock comprises, as glycols, at least MEG, MPG and 1,2-BDO. These glycols are typically present at a concentration in the range of from 0.1 to 30 wt % of the overall stream.

In such a reaction product stream, MEG is suitably present as at least 10 wt %, preferably as at least 30 wt % of the non-solvent fraction of the stream. MEG is suitably present as at most 95 wt %, preferably as at most 90 wt %, most preferably as at most 80 wt % of the non-solvent fraction of the stream.

In such a reaction product stream, MPG is suitably present as at least 2 wt %, preferably as at least 4 wt % of the non-solvent fraction of the stream. MPG is suitably present as at most 45 wt %, preferably as at most 20 wt % of the non-solvent fraction of the stream.

In such a reaction product stream, 1,2-BDO is suitably present as at least 1 wt %, preferably as at least 4 wt % of the non-solvent fraction of the stream. 1,2-BDO is suitably present as at most 20 wt %, preferably as at most 8 wt % of the non-solvent fraction of the stream.

As well as the glycols, the reaction product streams from hydrogenolysis reactions of saccharides may comprise water, oxygenates, hydrocarbons, catalyst, degradation products, and gases in any composition. The variety of compounds and their concentration depend on the saccharide-containing feedstock and the various hydrogenation and hydrogenolysis conversion conditions, including catalysts, reaction conditions such as temperature, pressure and saccharide concentration. However, suitably the hydrogenolysis reactions have gone to completion and the aqueous stream contains less than 5 wt %, preferably less than 2 wt %, more preferably less than 1 wt %, even more preferably less than 0.5 wt %, most preferably substantially no saccharides when considered as a weight percentage of the overall stream. Typically, the aqueous stream also contains less than 5 wt %, preferably less than 2 wt %, more preferably less than 1 wt %, even more preferably less than 0.5 wt %, most preferably substantially no glycerol, when considered as a weight percentage of the overall stream.

If the first mixture comprising MEG and 1,2-BDO in a first solvent is derived from such a reaction product stream, one or more treatment, separation and/or purification steps may be applied to the reaction product stream before the process of the present invention. Such steps may include one or more of: removal of at least a portion of the water present, for example by distillation; removal of light ends; fractional distillation to produce a glycols stream and removal of heavy organics and any inorganics present, such as catalyst material; and initial separation steps to achieve preliminary separation of glycols, e.g. separation of MPG by fractional distillation or other distillation process that results in a stream in which essentially all of the glycols remaining are MEG and 1,2-BDO.

The first solvent may be present in the first mixture due to its presence in the reaction product stream or may be added to a stream comprising MEG and 1,2-BDO in order to produce the first mixture. Preferably, the first solvent is the solvent in which the reaction to produce glycols is carried out. More preferably, the first solvent is water. The amount of first solvent present in the first mixture is suitably suitably at least 15 wt %, preferably at least 20 wt % and suitably at most 99.9 wt %, preferably at most 90 wt %, more preferably at most 80 wt % on the basis of the weight of the whole first mixture.

The second solvent comprises a hydrophobic solvent that suitably has a higher affinity for glycols than water. Also suitably, the second solvent has a higher affinity for 1,2-BDO than for MEG. Further, suitable solvents include those that show a liquid-liquid phase split when mixed with water or saline water at appropriate process temperatures, preferably in the range of from 0 to 250° C. In one embodiment, the second solvent has a higher boiling point then 1,2-BDO so that the glycol can be distilled off the solvent rather than vice versa.

In a preferred embodiment, the second solvent is an amine with a higher affinity for glycols than water and a higher affinity for 1,2-BDO than for MEG. Preferably, the amine comprises one or more alkyl amines. More preferably, the amine comprises a primary, a secondary, a tertiary alkyl amine, or a combination thereof. Preferably, the amine is a tertiary alkyl amine. Examples of suitable alkyl amines include paraffinic amines, naphthenic amines, aromatic amines, and mixtures thereof.

Preferably, the amine contains carbon and nitrogen atoms in a ratio of at most 8:1 (carbon:nitrogen atoms).

Preferably, the amine contains an aliphatic cyclic group either containing the amine nitrogen or attached to the amine nitrogen.

More preferably, the amine is selected from the group consisting of N,N-dimethylcyclohexylamine (DMCA), methyl cyclohexyl amine, N-methyl piperidine, triethylamine, tripropylamine, or a combination thereof.

Each 'extraction column' used in the process of the present invention may refer to a single column or to more than one column in series or parallel.

Further, the two or more 'extraction columns' used in the process may also form part of a single staged column with different feeds and outlets at different stages. Different sections of such a staged column may have different diameters.

The extraction columns used in the process of the present invention may be any suitable extraction units known in the art. State of the art extraction columns include, but are not limited to, agitated extraction columns, packed extraction columns, SCHEIBEL® Columns, KARR® Columns, rotating disc contactor (RDC) columns, pulsed, packed (SMVP) and sieve tray columns. In a preferred embodiment of the invention, the two streams are combined in a counter-current extraction column. In such a column, the two streams are fed to the unit at different points in the unit and are brought into contact with each other while passing through the column in a counter-current fashion.

The second solvent stream containing the second solvent may be combined with the first mixture, comprising MEG and 1,2-BDO in a first solvent, in any amount sufficient to allow a portion of the 1,2-BDO to dissolve in the second solvent. In certain embodiments, the amount of second solvent in the second solvent stream added to or combined with the first mixture comprising MEG and 1,2-BDO in a first solvent may suitably be at least 10 wt %, preferably at least 20 wt %, more preferably at least 30 wt % of the total amount of the total content of the first mixture. The amount of second solvent in the second solvent stream added to or combined with the first mixture comprising MEG and 1,2-BDO in a first solvent may suitably be at most 2000 wt %, preferably at most 500 wt %, more preferably at most 300 wt % of the total amount of the total content of the first mixture.

A second mixture of MEG and 1,2-BDO in the second solvent is recovered from the first extraction column. The molar ratio of MEG:1,2-BDO is lower in the second mixture (in the second solvent) than in the first mixture (in the first solvent). Preferably, the molar ratio of MEG:1,2-BDO in the second mixture (in the second solvent) is less than half, more preferably less than a quarter of that in the first mixture (in the first solvent).

A solution comprising MEG in the first solvent is also recovered from the first extraction column. The molar ratio of MEG:1,2-BDO in this solution is preferably at least 100:1, more preferably at least 200:1, most preferably at least 400:1.

The second mixture of MEG and 1,2-BDO in the second solvent is then combined with a first washing stream in a second extraction column. The first washing stream comprises the first solvent.

The second extraction column may be any suitable extraction units known in the art. State of the art extraction columns include, but are not limited to, agitated extraction columns, packed extraction columns, SCHEIBEL® Columns, KARR® Columns, rotating disc contactor (RDC) columns, pulsed, packed (SMVP) and sieve tray columns. In a preferred embodiment of the invention, the second mixture of MEG and 1,2-BDO in the second solvent is combined with the first washing stream in a counter-current extraction column. In such a column, the two streams are fed to the unit at different points in the unit and are brought into contact with each other while passing through the column in a counter-current fashion.

The first washing stream may be combined with the second mixture of MEG and 1,2-BDO in the second solvent in any amount sufficient to allow a portion, preferably a majority, most preferably essentially all of the MEG to dissolve in the first solvent present in the first washing stream. In certain embodiments, the amount of first solvent in the washing stream combined with the second mixture comprising MEG and 1,2-BDO in a second solvent may suitably be at least 10 wt %, preferably at least 20 wt %, more preferably at least 30 wt % of the total content of the second mixture comprising MEG and 1,2-BDO in a second solvent. The amount of first solvent in the washing stream combined with the second mixture comprising MEG and 1,2-BDO in a second solvent may suitably be at most 2000 wt %, preferably at most 500 wt %, more preferably at most 300 wt % of the total content of the second mixture comprising MEG and 1,2-BDO in a second solvent.

A first extract stream comprising the second solvent and 1,2-BDO is recovered from the second extraction column. Preferably, the ratio of 1,2-BDO:MEG in this stream is at least 20:1, more preferably at least 100:1, most preferably at least 200:1.

A third mixture of MEG and, optionally, 1,2-BDO in the first solvent is also recovered from the second extraction column. In a preferred embodiment of the invention, this mixture is provided to the first extraction column as a portion of the first mixture of MEG and 1,2-BDO in the first solvent.

Optionally, the solution comprising MEG in the first solvent recovered from the first extraction column is provided to a third extraction column and is combined therein with a further second solvent stream comprising the second solvent.

The third extraction column may be any suitable extraction units known in the art. State of the art extraction columns include, but are not limited to, agitated extraction columns, packed extraction columns, SCHEIBEL® Columns, KARR® Columns, rotating disc contactor (RDC) columns, pulsed, packed (SMVP) and sieve tray columns. In a preferred embodiment of the invention, the solution comprising MEG in the first solvent is combined with the further second solvent stream comprising the second solvent in a counter-current extraction column. In such a column, the two streams are fed to the unit at different points in the unit and are brought into contact with each other while passing through the column in a counter-current fashion.

The further second solvent stream comprising the second solvent may be combined with the solution comprising MEG in the first solvent in any amount sufficient to allow a portion, preferably a majority, most preferably essentially all of the MEG to dissolve in the further second solvent stream comprising the second solvent. In certain embodiments, the amount of second solvent in the further second solvent stream combined with the solution comprising MEG in the first solvent may suitably be at least 10 wt %, preferably at least 20 wt %, more preferably at least 30 wt % of the total content of the solution comprising MEG in the first solvent. The amount of second solvent in the further second solvent stream combined with the solution comprising MEG in the first solvent may suitably be at most 2000 wt %, preferably at most 500 wt %, more preferably at most 300 wt % of the total content of the solution comprising MEG in the first solvent.

In this case, a second extract stream comprising MEG in the second solvent is recovered. At least a portion of this second extract stream may then be separated in order to provide MEG. At least a portion of the stream may be used to provide the second solvent stream to the first extraction column.

Further, a first solvent stream comprising the first solvent is also recovered. Preferably, the first solvent stream is re-used as at least a portion of the first washing stream.

The present invention is further illustrated in the preferred, but non-limiting, embodiments of the invention illustrated in FIGS. 1 and 2. In these Figures, the first digit of each reference number refers to the Figure number (i.e. 1XX for FIG. 1 and 2XX for FIG. 2). The remaining digits refer to the individual features and the same features are provided with the same number in each Figure. Therefore, the same feature is numbered 104 in FIGS. 1 and 204 in FIG. 2.

In FIG. 1, a first mixture comprising MEG and 1,2-BDO in a first solvent is provided to a first extraction column 102. The first mixture comprising MEG and 1,2-BDO in a first solvent is formed from a combination of a feed 104 derived from the reaction product stream from a process for the hydrogenolysis of a saccharide-containing feedstock and a recycle stream comprising a third mixture comprising MEG and, optionally, 1,2-BDO in the first solvent 111 recovered from the second extraction column 101.

In the first extraction column 102, the first mixture is combined with a second solvent stream 105 comprising a second solvent. A solution 107 comprising MEG in the first solvent is recovered from the first extraction column 102. Also recovered is a second mixture 106 of MEG and 1,2-BDO in the second solvent. In the second mixture 106, the molar ratio of MEG:1,2-BDO is lower than in the first mixture.

The second mixture 106 is then combined with a first washing stream 109 comprising the first solvent in a second extraction column 101. A first extract stream 110 comprising the second solvent and 1,2-BDO is recovered from the second extraction column. Also recovered is the third mixture 111 comprising MEG and, optionally, 1,2-BDO in the first solvent.

In the embodiment of the invention illustrated in FIG. 2, a third extraction column 203 is included in the process. In this embodiment of the invention, the solution 207 comprising MEG in the first solvent is provided as a feed stream 212 to the third extraction column 203 and combined therein with a further second solvent stream 213 comprising the second solvent. A second extract stream 215 comprising the second solvent and MEG is recovered from the third extraction column 203. Part of this stream 216 is recycled to form the second solvent stream 205. A third solvent stream 214 comprising the first solvent is also recovered from the third extraction column 203.

That which is claimed is:

1. A process for the separation of monoethylene glycol (MEG) and 1,2-butanediol (1,2-BDO) from a first mixture comprising MEG and 1,2-BDO in a first solvent comprising water, by the steps of:
   (i) combining said first mixture with a second solvent stream comprising a second solvent comprising one or more alkyl amines in a first extraction column;
   (ii) recovering (a) a second mixture of MEG and 1,2-BDO in the second solvent, wherein the molar ratio of MEG:1,2-BDO is lower in the second mixture than in the first mixture; and (b) a solution comprising MEG in the first solvent;
   (iii) combining said second mixture with a first washing stream, said first washing stream also comprising the first solvent in a second extraction column;
   (iv) recovering (c) a first extract stream comprising the second solvent and 1,2-BDO and (d) a third mixture comprising MEG and, optionally, 1,2-BDO in the first solvent.

2. A process according to claim 1, wherein the third mixture comprising MEG and, optionally, 1,2-BDO in the first solvent is provided to the first extraction column as a portion of the first mixture of MEG and 1,2-BDO in the first solvent.

3. A process according to claim 1, further comprising the step of:
   (v) providing the solution comprising MEG in the first solvent as a feed stream to a third extraction column and combining it therein with a further second solvent stream comprising the second solvent; and recovering (e) a second extract stream comprising the second solvent and MEG; and (f) a first solvent stream comprising the first solvent.

4. A process according to claim 3, wherein at least a portion of the second extract stream comprising the second solvent and MEG is provided to the first extraction column as at least a portion of the second solvent stream comprising a second solvent.

5. A process as claimed in claim 1, wherein the first mixture comprising MEG and 1,2-BDO is derived from the reaction product stream from a process for the hydrogenolysis of a saccharide-containing feedstock.

6. A process according to claim 1, wherein the one or more alkyl amine contains carbon and nitrogen atoms in a ratio of at most 8:1.

7. A process according to claim 1, wherein the one or more alkyl amine contains an aliphatic cyclic group either containing the amine nitrogen or attached to the amine nitrogen.

* * * * *